United States Patent
Lashinski

(10) Patent No.: US 10,743,977 B2
(45) Date of Patent: Aug. 18, 2020

(54) INTRAVASCULAR BLOOD FILTER

(71) Applicant: Claret Medical, Inc., Santa Rosa, CA (US)

(72) Inventor: Randall T. Lashinski, Windsor, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 290 days.

(21) Appl. No.: 15/838,949

(22) Filed: Dec. 12, 2017

(65) Prior Publication Data

US 2018/0177582 A1 Jun. 28, 2018

Related U.S. Application Data

(63) Continuation of application No. 13/738,847, filed on Jan. 10, 2013, now abandoned, which is a continuation of application No. 12/689,997, filed on Jan. 19, 2010, now Pat. No. 8,372,108.

(60) Provisional application No. 61/145,149, filed on Jan. 16, 2009.

(51) Int. Cl.
*A61F 2/01* (2006.01)

(52) U.S. Cl.
CPC ............... *A61F 2/013* (2013.01); *A61F 2/01* (2013.01); *A61F 2002/018* (2013.01); *A61F 2230/0006* (2013.01); *A61F 2230/0008* (2013.01); *A61F 2230/0067* (2013.01); *A61F 2230/0069* (2013.01)

(58) Field of Classification Search
CPC ...... A61F 2/012; A61F 2/01; A61F 2002/018; A61F 2230/0006; A61F 2230/0008; A61F 2230/0067; A61F 2230/0069; A61F 2/013; A61F 6/225

See application file for complete search history.

(56) References Cited

U.S. PATENT DOCUMENTS

| | | |
|---|---|---|
| 3,472,230 A | 10/1969 | Fogarty |
| 4,619,246 A | 10/1986 | Molgaard-Nielsen et al. |
| 4,630,609 A | 12/1986 | Chin |
| 4,650,466 A | 3/1987 | Luther |

(Continued)

FOREIGN PATENT DOCUMENTS

| | | |
|---|---|---|
| DE | 10049812 | 4/2002 |
| EP | 1400257 A2 | 3/2004 |

(Continued)

OTHER PUBLICATIONS

Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).

(Continued)

*Primary Examiner* — Erich G Herbermann

(74) *Attorney, Agent, or Firm* — Seager, Tufte & Wickhem LLP

(57) ABSTRACT

Disclosed is a novel filter and delivery means. The device described within will not interfere with standard practice and tools used during standard surgical procedures and tools such as cannulas, clamps or dissection instruments including valve replacement sizing gages or other surgical procedures where the patient must be put on a heart-lung machine cross-clamping the aorta.

11 Claims, 18 Drawing Sheets

(56) References Cited

U.S. PATENT DOCUMENTS

| | | |
|---|---|---|
| 4,706,671 A | 11/1987 | Weinrib |
| 4,723,549 A | 2/1988 | Wholey |
| 4,873,978 A | 10/1989 | Ginsburg |
| 5,108,419 A | 4/1992 | Reger |
| 5,192,286 A | 3/1993 | Phan |
| 5,200,248 A | 4/1993 | Thompson et al. |
| 5,329,923 A | 7/1994 | Lundquist |
| 5,348,545 A | 9/1994 | Shani et al. |
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,680,873 A | 10/1997 | Berg et al. |
| 5,707,389 A | 1/1998 | Louw et al. |
| 5,766,151 A | 6/1998 | Valley et al. |
| 5,779,716 A | 7/1998 | Cano et al. |
| 5,814,064 A | 9/1998 | Daniel |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates |
| 6,120,494 A | 9/2000 | Jonkman |
| 6,126,673 A | 10/2000 | Kim et al. |
| 6,129,739 A | 10/2000 | Khosravi |
| 6,142,987 A | 11/2000 | Tsugita |
| 6,146,396 A | 11/2000 | Konya et al. |
| 6,152,946 A | 11/2000 | Broome et al. |
| 6,171,328 B1 | 1/2001 | Addis |
| 6,179,851 B1 | 1/2001 | Barbut et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika |
| 6,336,934 B1 | 1/2002 | Gilson et al. |
| 6,346,116 B1 | 2/2002 | Brooks et al. |
| 6,361,545 B1 | 3/2002 | Macoviak et al. |
| 6,364,900 B1 | 4/2002 | Heuser |
| 6,371,970 B1 | 4/2002 | Khosravi et al. |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson et al. |
| 6,440,120 B1 | 8/2002 | Maahs |
| 6,454,799 B1 | 11/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,558,356 B2 | 5/2003 | Barbut |
| 6,589,263 B1 | 7/2003 | Hopkins et al. |
| 6,595,983 B2 | 7/2003 | Voda |
| 6,605,102 B1 | 8/2003 | Mazzocchi |
| 6,616,679 B1 | 9/2003 | Khosravi et al. |
| 6,620,148 B1 | 9/2003 | Tsugita |
| 6,620,182 B1 | 9/2003 | Khosravi et al. |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,306,618 B2 | 12/2007 | Demond et al. |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,722,634 B2 | 5/2010 | Panetta et al. |
| 7,766,961 B2 | 8/2010 | Patel et al. |
| 7,922,732 B2 | 3/2011 | Mazzocchi et al. |
| 7,918,859 B2 | 4/2011 | Katoh et al. |
| 7,976,562 B2 | 7/2011 | Bressler et al. |
| 7,998,104 B2 | 8/2011 | Chang |
| 8,002,790 B2 | 8/2011 | Brady et al. |
| 8,021,351 B2 | 9/2011 | Boldenow et al. |
| 8,052,713 B2 | 11/2011 | Khosravi et al. |
| 8,092,483 B2 | 1/2012 | Galdonik et al. |
| 8,372,108 B2 | 2/2013 | Lashinski |
| 8,382,788 B2 | 2/2013 | Galdonik |
| 8,460,335 B2 | 6/2013 | Carpenter |
| 8,518,073 B2 | 8/2013 | Lashinski |
| 8,753,370 B2 | 6/2014 | Lashinski |
| 8,876,796 B2 | 11/2014 | Fifer et al. |
| 8,974,489 B2 | 3/2015 | Lashinski |
| 9,017,364 B2 | 4/2015 | Fifer et al. |
| 9,055,997 B2 | 6/2015 | Fifer et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 9,480,548 B2 | 11/2016 | Carpenter |
| 9,492,264 B2 | 11/2016 | Fifer et al. |
| 9,566,144 B2 | 2/2017 | Purcell et al. |
| 9,636,205 B2 | 5/2017 | Lee et al. |
| 9,943,395 B2 | 4/2018 | Fifer et al. |

(56) References Cited

U.S. PATENT DOCUMENTS

| | | |
|---|---|---|
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1* | 11/2002 | Barbut .............. A61F 2/013 606/194 |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1* | 7/2006 | Barbut .............. A61F 2/013 623/1.15 |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 7/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0211095 A1 | 8/2010 | Carpenter |
| 2010/0228280 A1 | 9/2010 | Groothuis et al. |
| 2010/0312268 A1 | 12/2010 | Belson |
| 2010/0324589 A1 | 12/2010 | Carpenter et al. |
| 2011/0066221 A1 | 3/2011 | White et al. |
| 2012/0046739 A1 | 2/2012 | Von Oepen et al. |
| 2012/0095500 A1 | 4/2012 | Heuser |
| 2012/0172916 A1 | 7/2012 | Fifer et al. |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0100597 A1 | 4/2014 | Wang et al. |
| 2014/0282379 A1 | 9/2014 | Lee et al. |
| 2015/0039016 A1 | 2/2015 | Naor et al. |
| 2015/0209131 A1 | 7/2015 | Fifer et al. |
| 2015/0230910 A1 | 8/2015 | Lashinski et al. |
| 2015/0335416 A1 | 11/2015 | Fifer et al. |
| 2016/0058541 A1 | 3/2016 | Schotzko et al. |
| 2016/0262864 A1 | 9/2016 | Von Mangoldt et al. |
| 2016/0310255 A1 | 10/2016 | Purcell et al. |
| 2017/0042658 A1 | 2/2017 | Lee et al. |
| 2017/0112609 A1 | 4/2017 | Purcell et al. |
| 2017/0181834 A1 | 6/2017 | Fifer et al. |
| 2017/0202657 A1 | 7/2017 | Lee et al. |

FOREIGN PATENT DOCUMENTS

| | | |
|---|---|---|
| EP | 1253871 | 2/2007 |
| EP | 2303384 | 4/2011 |
| EP | 2391303 | 12/2011 |
| EP | 2480165 | 8/2012 |
| EP | 2658476 | 11/2013 |
| EP | 2387427 | 8/2014 |
| JP | 2003-505216 | 2/2003 |
| JP | 2003-526451 | 9/2003 |
| JP | 2003-290231 | 10/2003 |
| JP | 3535098 B2 | 6/2004 |
| JP | 2006-500187 | 1/2006 |
| JP | 2008-511401 | 4/2008 |
| JP | 2008-515463 | 5/2008 |
| JP | 2011-525405 A | 9/2011 |
| WO | WO 99/23976 | 5/1999 |
| WO | WO 01/67989 | 9/2001 |
| WO | WO 2004/026175 | 4/2004 |
| WO | WO 2005/118050 | 12/2005 |
| WO | WO 2006/026371 | 3/2006 |
| WO | WO 2008/033845 | 3/2008 |
| WO | WO 2008/100790 | 8/2008 |
| WO | WO 2008/113857 | 9/2008 |

(56) References Cited

FOREIGN PATENT DOCUMENTS

| WO | WO 2009/032834 | | 3/2009 |
|---|---|---|---|
| WO | WO 2010/008451 | | 1/2010 |
| WO | WO 2010/081025 | | 7/2010 |
| WO | WO 2010/083527 | A2 | 7/2010 |
| WO | WO 2010/088520 | A2 | 8/2010 |
| WO | WO 2011/034718 | A2 | 3/2011 |
| WO | WO 2011/017103 | A2 | 10/2011 |
| WO | WO 2012/092377 | A1 | 7/2012 |

OTHER PUBLICATIONS

Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).

Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).

Office Action for U.S. Appl. No. 15/080,345 dated Jan. 12, 2018, in 13 pages.

Final Office Action for U.S. Appl. No. 12/689,997 dated Nov. 5, 2012, in 11 pages.

Final Office Action for U.S. Appl. No. 12/871,708 dated May 28, 2014, in 31 pages.

Final Office Action for U.S. Appl. No. 13/497,235 dated Oct. 22, 2015 in 34 pages.

International Search Report in Application No. PCT/US2010/021417 dated Aug. 23, 2010, in 4 pages.

International Search Report in Application No. PCT/US2010/047166 dated Apr. 27, 2011, in 7 pages.

Notice of Allowance for U.S. Appl. No. 12/689,997 dated Jan. 9, 2013, in 9 pages.

Notice of Allowance for U.S. Appl. No. 12/871,708 dated Dec. 23, 2015, in 16 pages.

Notice of Allowance for U.S. Appl. No. 13/497,235 dated Jan. 6, 2017, in 16 pages.

Office Action for U.S. Appl. No. 12/689,997 dated Apr. 4, 2012, in 13 pages.

Office Action for U.S. Appl. No. 12/871,708 dated Oct. 11, 2013, in 34 pages.

Office Action for U.S. Appl. No. 12/871,708 dated Mar. 12, 2015, in 36 pages.

Office Action for U.S. Appl. No. 13/497,235 dated Apr. 2, 2015, in 21 pages.

Office Action for U.S. Appl. No. 13/497,235 dated Jun. 15, 2016, in 25 pages.

Supplementary European Search Report in Application No. PCT/US2010/021417 dated Nov. 28, 2012, in 5 pages.

Final Office Action for U.S. Appl. No. 13/738,847 dated Sep. 11, 2015 in 12 pages.

Final Office Action for U.S. Appl. No. 13/738,847 dated Sep. 13, 2017 in 10 pages.

Office Action for U.S. Appl. No. 13/738,847 dated Apr. 29, 2015, in 16 pages.

Office Action for U.S. Appl. No. 13/738,847 dated May 20, 2016, in 9 pages.

Office Action for U.S. Appl. No. 13/738,847 dated Jan. 23, 2017, in 6 pages.

Office Action for U.S. Appl. No. 13/738,847 dated May 10, 2017, in 11 pages.

\* cited by examiner

INTRAVASCULAR BLOOD FILTER

CROSS-REFERENCE TO RELATED APPLICATIONS

This application is a continuation of U.S. application Ser. No. 13/738,847, filed Jan. 10, 2013, which is a continuation of U.S. application Ser. No. 12/689,997, filed Jan. 19, 2010, now U.S. Pat. No. 8,372,108, which claims priority benefit under 35 U.S.C. § 119(e) to U.S. Provisional Application No. 61/145,149, filed Jan. 16, 2009, entitled "Intravascular Blood Filter," all of which applications are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

This invention relates generally to medical devices used during vascular intervention, and more particularly, concerns medical devices that are useful in treating aortic valve replacement, thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

Percutaneous aortic valve replacement has been in development for some time now and stroke rates related to this procedure are between four and twenty percent. During catheter delivery and implantation plaque may be dislodged from the vasculature. The invention contained within will block the emboli from traveling through the carotid circulation and onto the brain. When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exist retrieval devices for the removal of foreign bodies, certain of such devices form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another distal vessel.

Various thrombectomy and foreign matter removal devices have been disclosed in the art. However, such devices have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, wherein the pleats extend radially and can obstruct retraction of the device into the micro catheter sheathing.

What has been needed and heretofore unavailable is an extraction device that can be easily and controllably deployed into and retracted from the circulatory system for the effective removal of clots and foreign bodies. There is also a need for a system that can be used as a temporary arterial or venous filter to capture and remove thromboemboli generated during endovascular procedures. Moreover, due to difficult-to-access anatomy such as the cerebral vasculature and the neurovasculature, the invention should possess a small collapsed profile and preferably be expandable to allow the device to be delivered through the lumen of commercially available catheters. The present invention satisfies these needs.

SUMMARY OF THE INVENTION

Most filter devices are delivered from the groin and are placed distal to the flow of the lesion or site in question.

Single basket-type filters or Nitinol loop filters are the most common used today in carotid stent procedures of vein graft stenting. As the guidewire is delivered past the lesion the filter is delivered over the guidewire protecting the distal vasculature. The invention here may be delivered from the groin in a conventional manner to vessels such as the carotid arteries or via radial (arm vasculature) approach. Protecting the carotid arteries and cerebral vasculature system is the main goal while leaving the aortic arch free from catheters and wire as much as possible during the delivery of other devices such as aortic balloons and prosthetic valves or other associated devices.

One method of filtering the carotid arteries leaving the aorta free from obstruction is to deliver a filter to each of the carotid arteries from the groin leaving them in the carotid vasculature and retrieving them via snare post procedure. A delivery catheter would be inserted through an introducer in the groin (femoral artery) and delivered to the common carotid arteries and detached. The delivery catheter would be removed and a second filter would be delivered in a similar manner to the other carotid artery. With two detached filters now in place the procedure treating the aortic or mitral valve can now be completed with embolic protection for the cerebral vascular system. Once the procedure to the valve is completed, the filters can be snared and retrieved back out the femoral artery as they were delivered. Any embolic particles will be captured in the filter device and removed safely from the body.

Another method for filtering the carotid arteries would be to deliver a filter from the femoral artery and utilize a single catheter to house the two attachment means to the filters. These attachments may be a wire similar to a guidewire or a hypo-tube to connect the filter element to an external portion of the body. Keeping these wires or connection means organized and contained within a single or dual lumen catheter will help organize and limit potential entanglement with other catheters being delivered to the target site such as the aortic valve or other cardiac elements including but not limited to the mitral valve and coronary arteries. The distal portion of the catheter may have a single exit portion or a staggered exit to allow an exit at different points along the catheter. One exit port may be at the distal most end of the catheter and the other may be a centimeter proximal from this to allow the attachment wire to exit near the left common carotid artery. Furthermore, there could be an extension to the distal most portion of the catheter allowing side ports for both wires to exit. This would allow for additional catheter stabilization within the aorta.

Another embodiment would deliver filters to the carotid from the radial artery and allow for a clear aortic arch from catheters and other delivery means from a more conventional femoral delivery means. From this access site a plurality of filters could be delivered through a common access sheath or the filters could be delivered from a dual lumen catheter with each lumen housing a single filter.

Another delivery means would utilize a single catheter with filters mounted in a coaxial manner where the distal filter would be delivered first and could be mounted to a wire where the second would be mounted to a hypo-tube where the first filters wire would run through the second allowing for relative motion between the two filters. The first filter would be delivered to the left common carotid from the radial artery and the second would be delivered to the right common carotid artery or the brachiocephalic trunk in a coaxial manner. These filters would be opposed in direction as the distal filter would be filtering blood flowing from the base of the aorta to the head and toward the distal end of the guidewire. The proximal filter would be filtering blood from the base of the aorta to the head and toward the proximal end of the guidewire. Placing the two filters together there would be a conical shape configuration where the large diameter portions of the cones would meet. These two filters would be delivered in a collapsed configuration and expanded when expelled from the delivery catheter. Retrieval would be a retraction of the filter back into a recovery catheter that would be a larger inner diameter than the delivery catheter to allow room for particulate. Being opposed in capture direction the right carotid would be the first filter that would be recovered by an expanded sheath where the embolic material would not be disturbed and further withdrawn to a smaller sheath for removal from the body. The expanded sheath could be constructed from braided Nitinol wire pre-shaped so when exposed the braid would expand to receive the filter without squeezing out any trapped emboli. The second or left carotid filter would be recovered in a conventional manner where the larger diameter would be pulled into a sheath to trap and remove the emboli within the tailor distal portion of the filter.

Another means to deliver the filters via radial artery approach would be to utilize a dual lumen catheter where each lumen would house a single filter. The first lumen would deliver a filter to the left carotid artery and the second lumen would deliver a filter to the right carotid artery. The lumens could be staggered in length to reach each ostium in which case the first or left filter lumen would be longer in length to allow for placement distal from the second filter placement in the right carotid. Additionally, the second lumen may be pre-shaped with a curve to allow easy access to the right carotid artery. This pre-shaped curve may be retained in a straighter manner to allow for delivery and released to express the delivery shape when at the bifurcation of the subclavian and the carotid artery. Furthermore, there may be an active shaping where the curve is directed external to the body by a handle mechanism such as a pull-wire where tension would generate a compressive force to the catheter column preferentially bending the lumen. Recovery could utilize the same dual lumen concept or utilize a second recovery sheath independently from one another.

Another application for this device and method would be for surgical operations where the patient may be put on heart-lung bypass. During cross clamping of the aorta catheters or wires in the aorta may interfere with the procedure and allow leakage of blood around the cannulas used. If any of the above described devices or techniques are used before the patient's chest is opened this filtration of the carotid vessels would protect from emboli thus reducing the stroke risk during and after the procedure. Additional anti thrombotic coatings to the filter could allow for an extended implantation time allowing filtration time to be extended post procedure. An example of this coating would be Heparin. Placement of these catheters and filters could be under fluoroscopy or ultrasound guidance to direct proper filter placement. Radiopaque markers may add necessary visibility to the catheter, filter and or wires.

Another surgical delivery means would be an insertion to the carotid artery via the neck. The filter could face either antigrade or retrograde depending upon the placement insertion point or access site. This would allow for complete filtration without any aortic interference as the entire devices would be within the carotid circulation. With this delivery technique the puncture site would be very small and recovery could be through the entry site or through the groin as the filter could be inserted distal to meet a recovery sheath in the aorta. With this groin recovery any emboli within the proximal carotid would be captured before later dislodgement.

Intravascular filters have been used in many configurations ranging from a windsock style as commercialized as the FilterWire from Boston Scientific or the ACCUNET from Abbott Vascular or the Spider from eV3. These filters utilize a memory metal such as Nitinol is used to oppose the vascular wall tightly sealing any emboli from passage while a filter material such as a porous fabric material retains and emboli from passing distally from the device. Another example is a laser cut memory metal where the basket is the frame and the filter is used to trap emboli when expanded. Another example is constructed from a braided wire such as Medtronic's Interceptor PLUS where once exposed the braid expands to create a funnel or cone shape to trap emboli and the proximal or larger end is pre-shaped to accept blood flow with larger openings heat-set into the memory metal such as Nitinol. These filters range in diameter from about 2-15 mm in diameter and are approximately 20-30 mm in length. They are generally attached to a guidewire and sheathed for delivery and resheathed for recovery. The catheter profile measures about 1 to 2 mm in diameter and has a length of about 90 to 200 cm. Catheter construction is normally a polypropylene or polyethylene material but nylons and blends can be used as well. All devices are considered single use and are commonly placed for carotid stenting or savenous vein grafts stenting.

DETAILED DESCRIPTION OF THE PREFERRED EMBODIMENT

Figure 1:
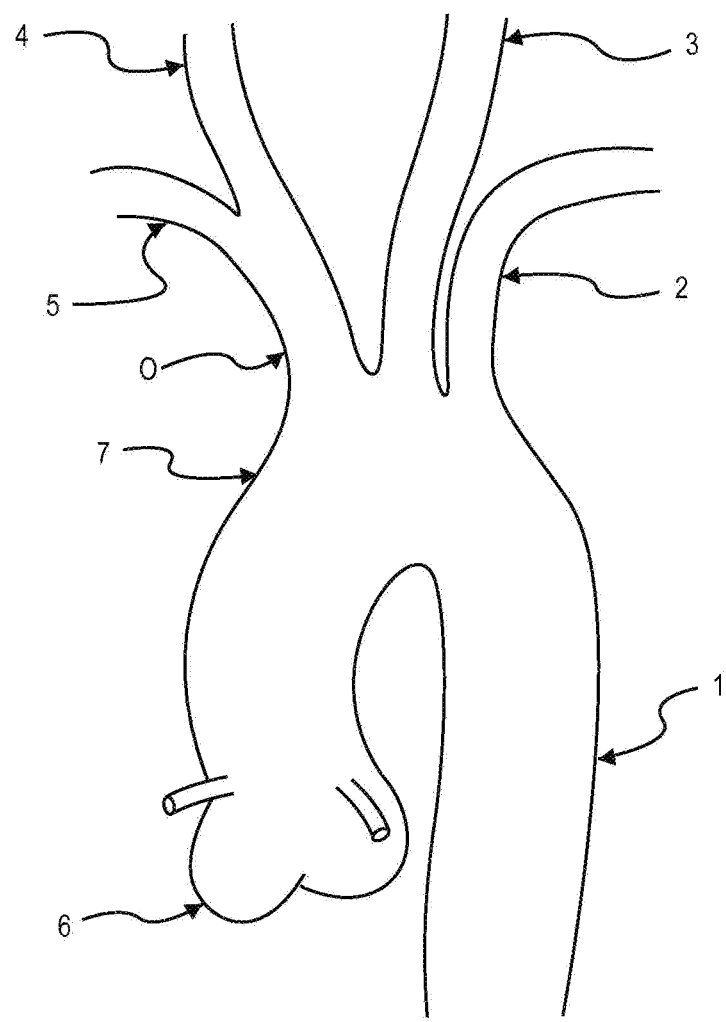
FIG. 1 illustrates the vascular anatomy of the aorta and surrounding great vessels.
Figure 2:
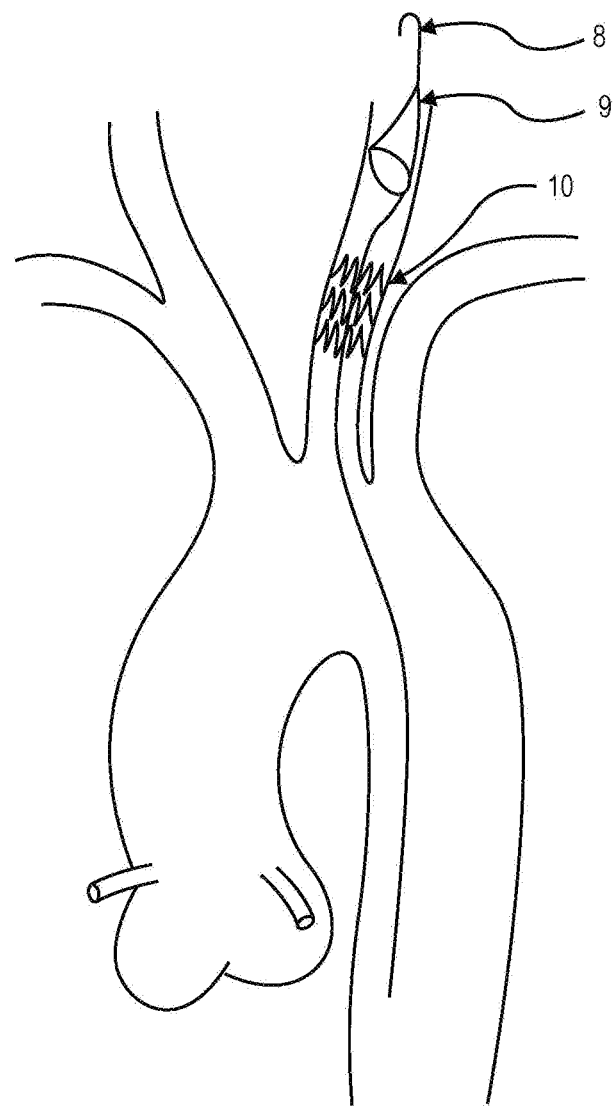
FIG. 2 illustrates the common technique in carotid filter 8 insertion for carotid stenting 10 as delivered via femoral artery over a guidewire 9.
Figure 3:
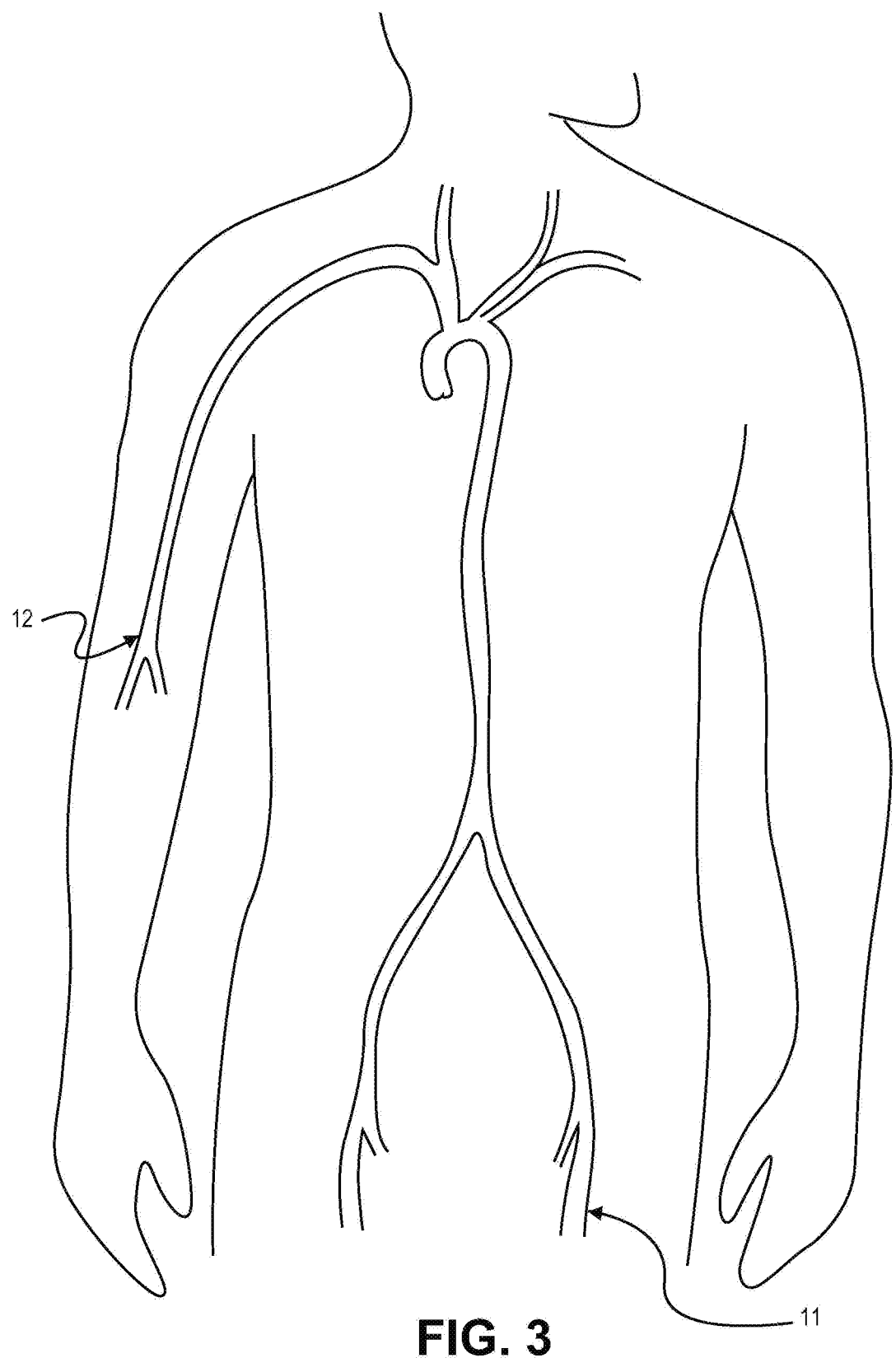
FIG. 3 illustrates the aortic vasculature where sheaths could be placed by the interventional cardiologist. The right femoral 11 being the most common access as the cardiologist works from the right side of the patient which is presented to the physician while on the table. The right radial artery 12 has been used but due to the small diameter of the vessel is not a common insertion point for the cardiologist.
Figure 4:
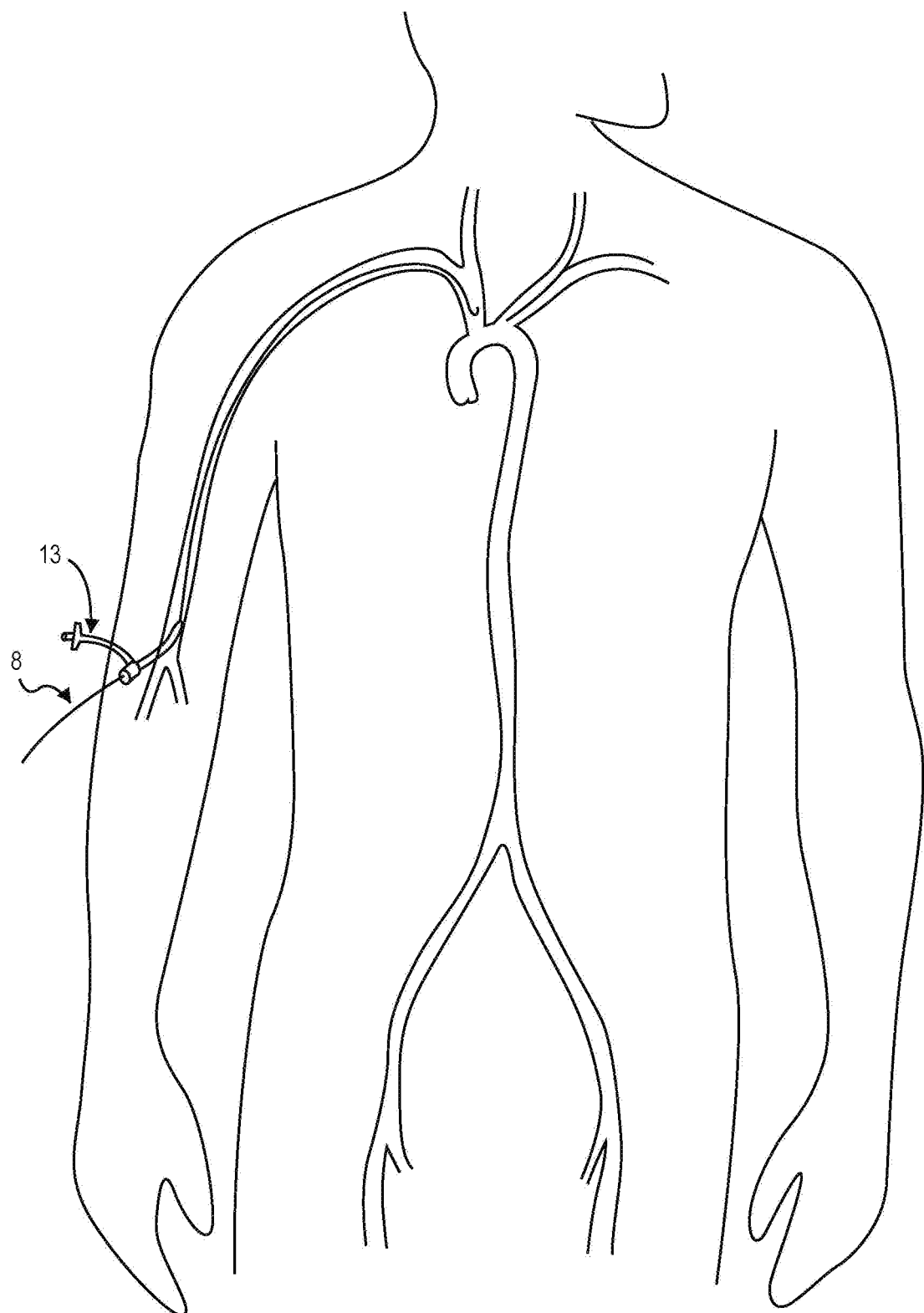
FIG. 4 illustrates a brachial entry with common introducer 13 and guidewire 8 techniques.
Figure 5:
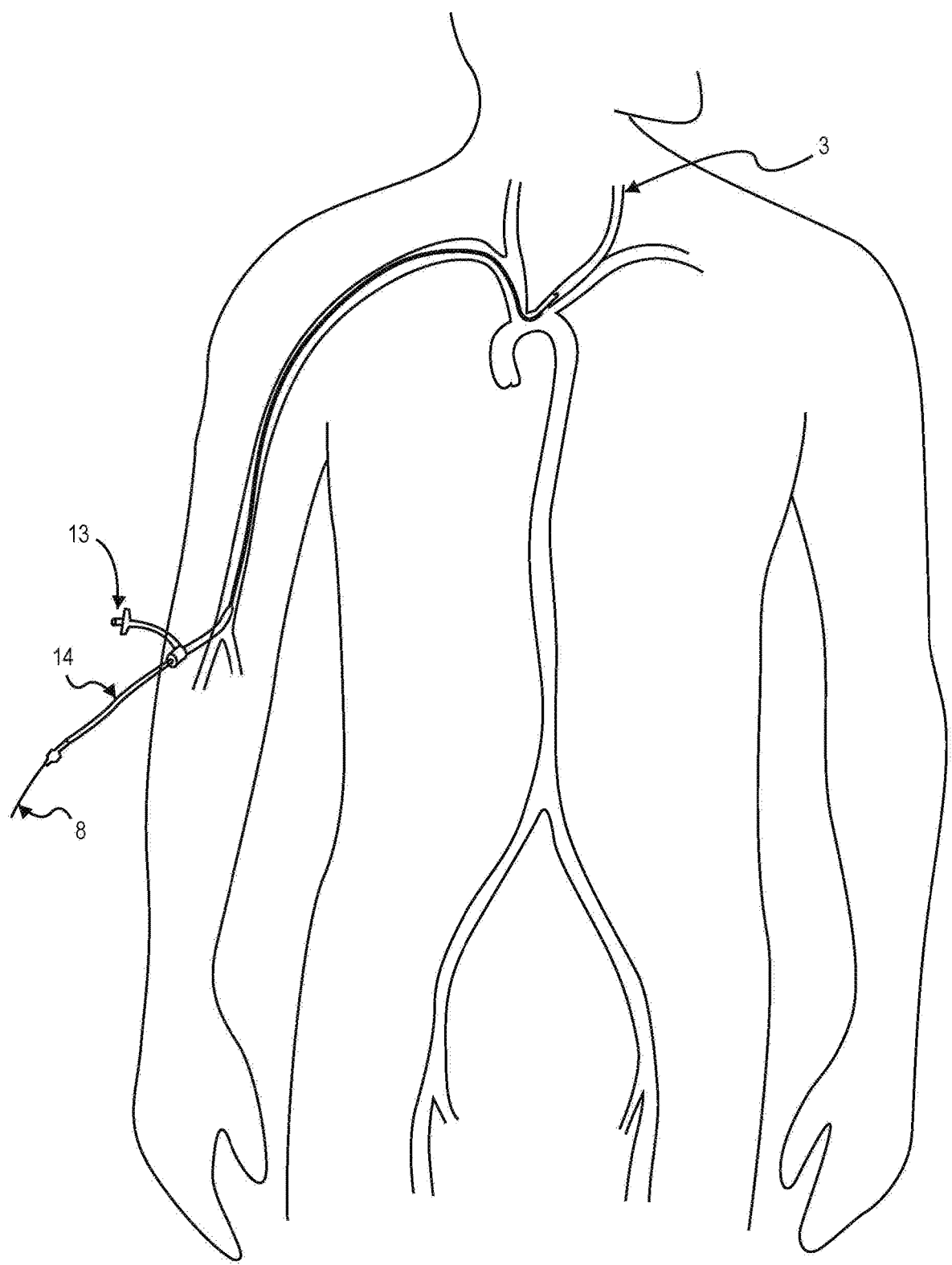
FIG. 5 illustrates the guide catheter 14 being inserted to the introducer 13 over the guidewire 8 in a brachial artery entry where the guide catheter 14 has a preshaped distal section to access the left common carotid 3.
Figure 6:
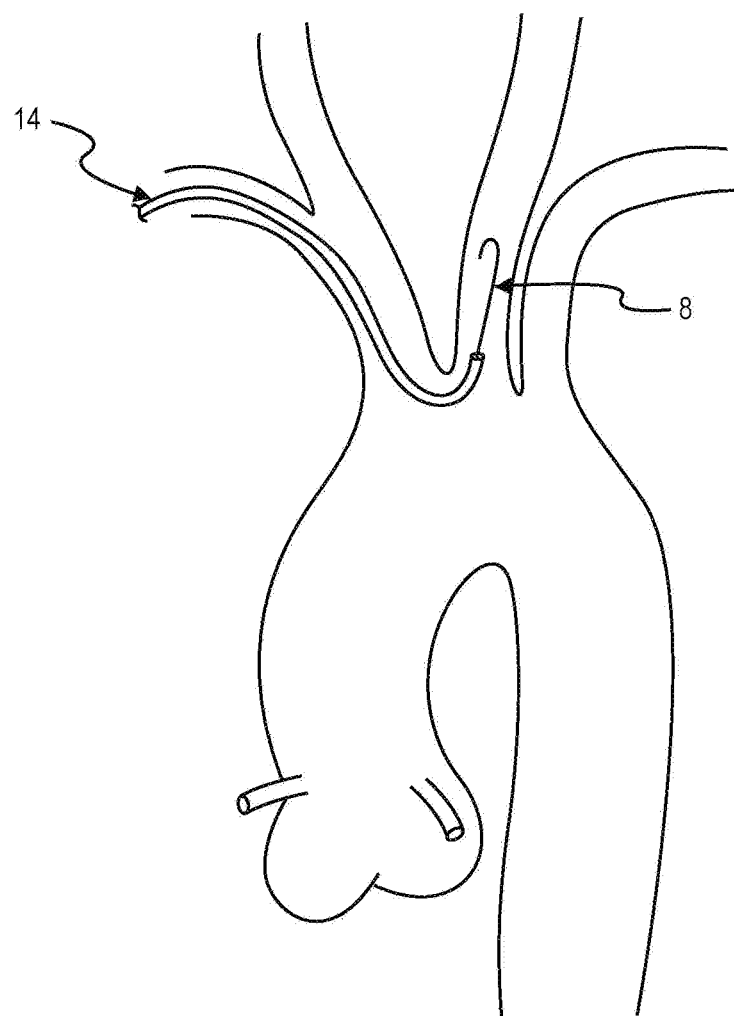
FIG. 6 illustrates a closer view of the guide catheter 14 and guidewire 8 accessing the left carotid artery where the first filter would be placed.
Figure 7:
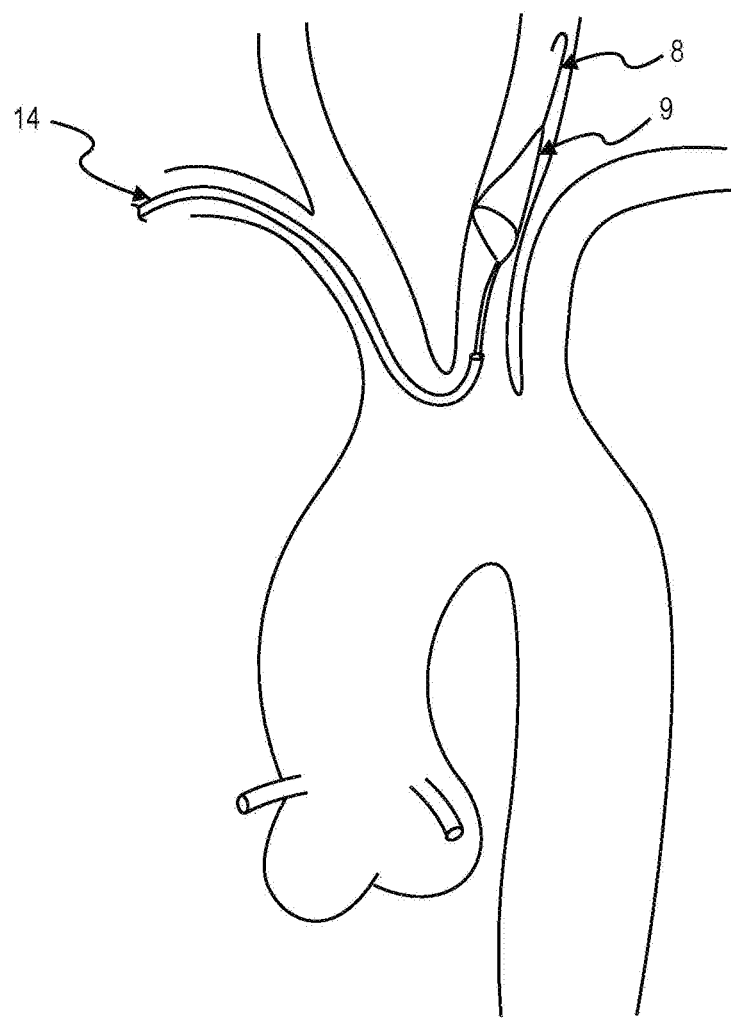
FIG. 7 illustrates the deployment of the first filter 9 through the guide catheter 14 over a guidewire 8 where the filter 9 is fully opposed to the left carotid artery.
Figure 8:
FIG. 8 illustrates both filters 9 deployed and protecting the carotid arteries utilizing a common guidewire 8 and common guide catheter 14.
Figure 9:
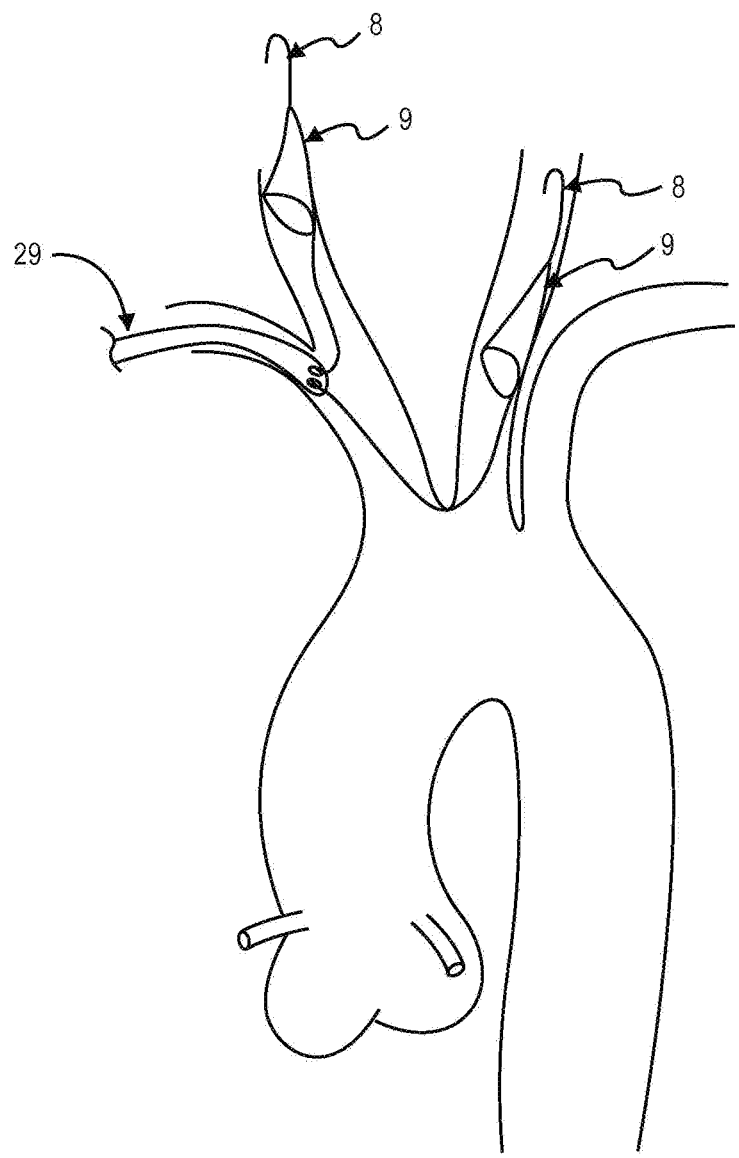
FIG. 9 illustrates a dual lumen catheter 29 where each filter 9 has a single guidewire 8. Both filters 9 are in a conventional orientation where the flow is in the distal direction or toward the distal tip of the guidewire 8. Independent recovery of the filters 9 could occur or a common recovery sheath may be used to load both into one sheath.
Figure 10:
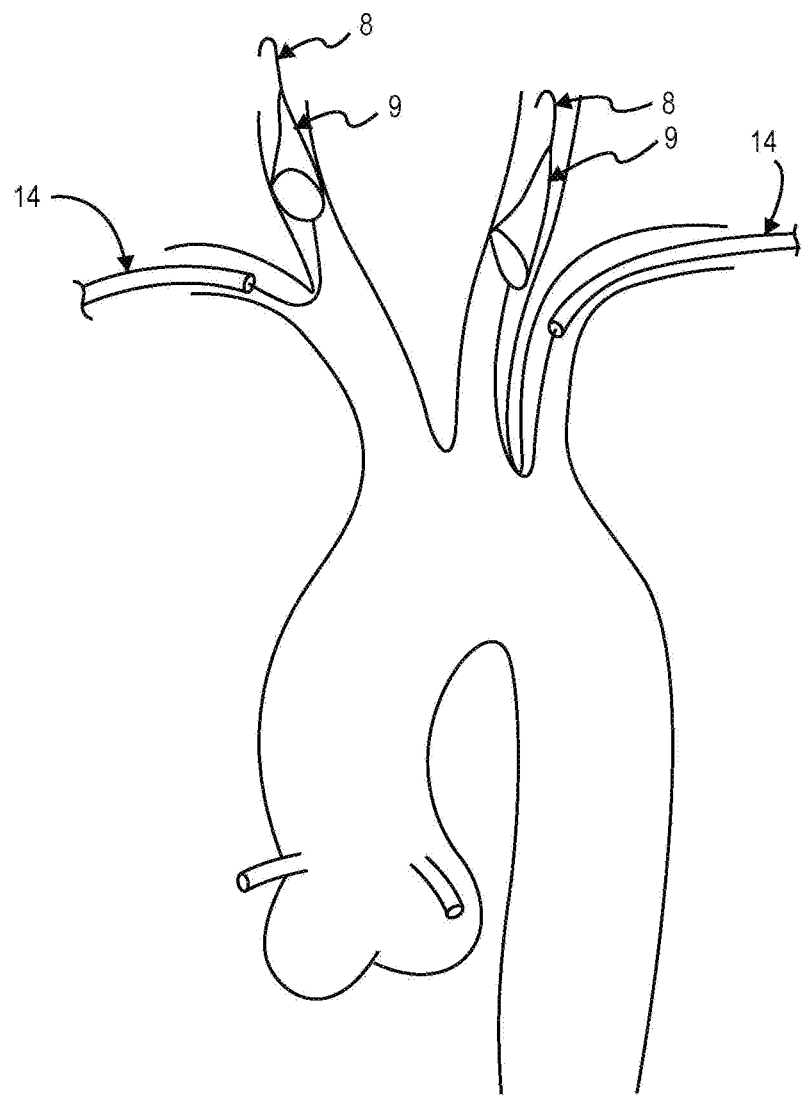
FIG. 10 illustrates both filters 9 being delivered via subclavian where the left filter is delivered via left subclavian artery with an entry point in the radial artery. Each delivery would include a guidewire 8 and a guide catheter 14 where a pre-shaped curve would allow access into the respective carotid artery.
Figure 11:
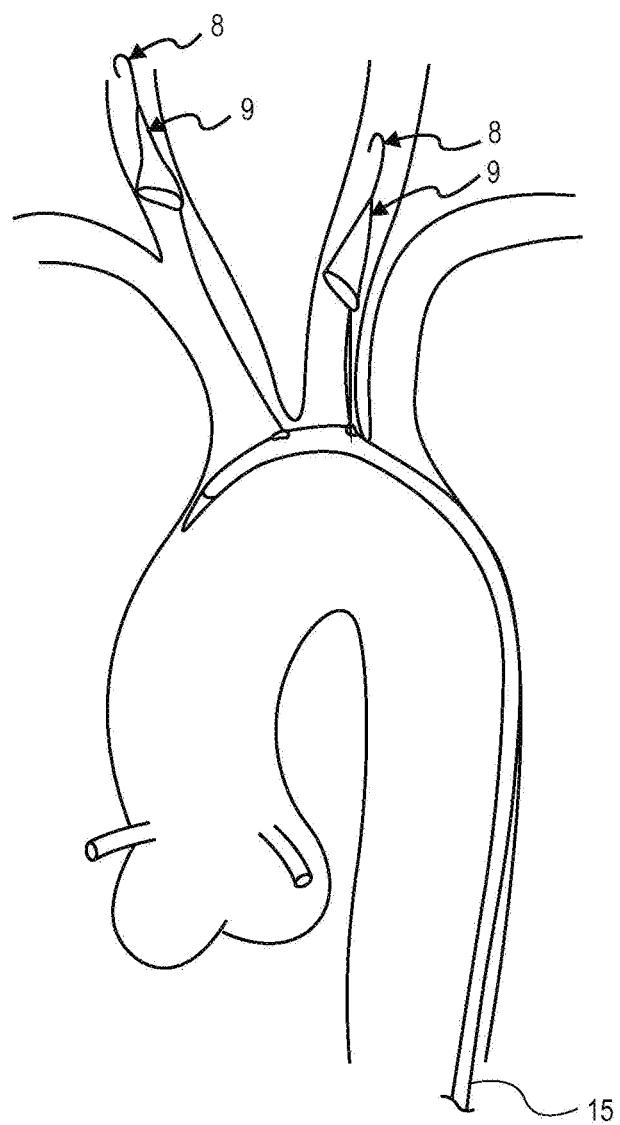
FIG. 11 illustrates a single organization catheter 15 to retain two filter 9 guidewires 8 controlling the potential for entanglement with each wire or other catheters introduced to the body. These catheters would include pigtail catheters used for contrast injections, balloon catheters for dilation or other catheters for delivery of therapeutic agents or implantable devices such as stents or prosthetic heart valves where the catheters are generally larger (18-26 French) in diameter. The catheter would have two distal exit ports to allow each filter to exit at the respective ostia. A distal section would extend beyond the brachiocephalic trunk allowing for a smooth shape to the catheter and ensure it is close to the outer radius of the arch.
Figure 12:
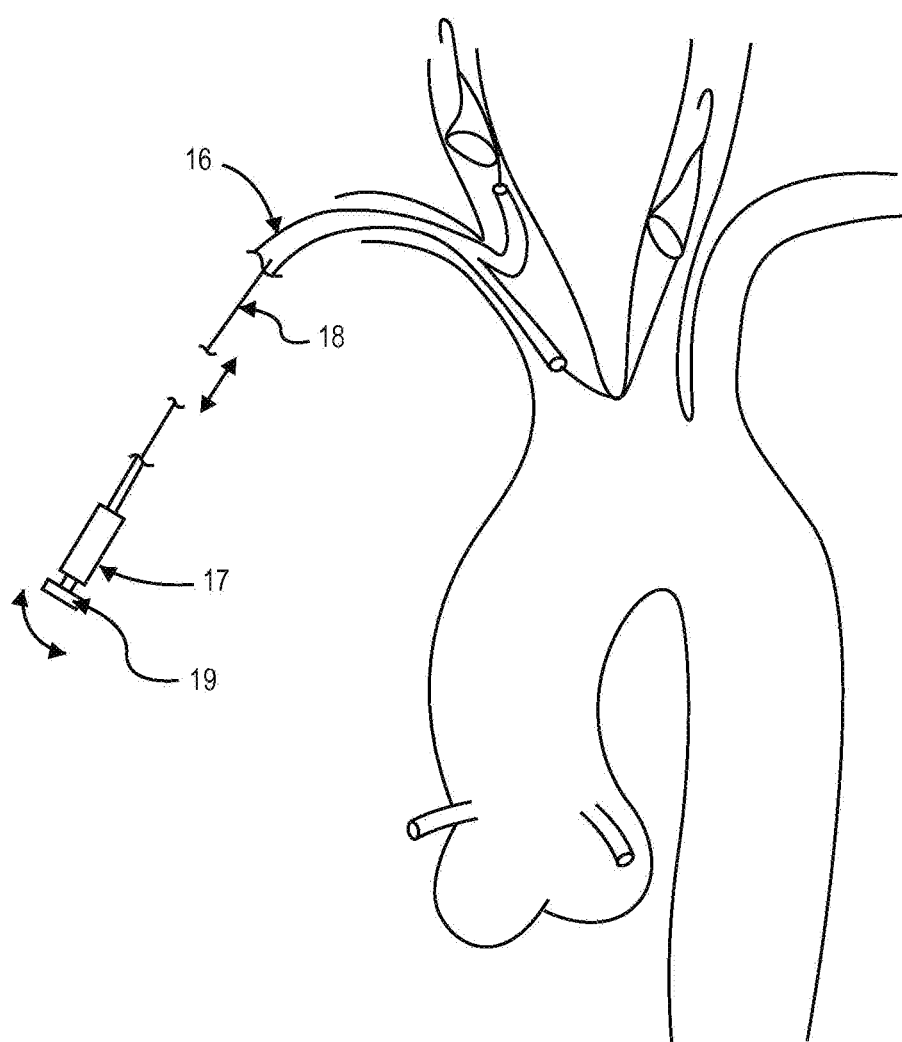
FIG. 12 illustrates a dual lumen catheter 16 with an active curving mechanism to steer each lumen to the respected carotid artery. The deflection will allow for active steering of each distal section to account for any differences in anatomy from patient to patient. Similar to electrophysiology catheters a deflection wire 18 could be tensioned to provide a bias or curve to tip. The delivery of each filter would be in a conventional orientation where the blood flow would be in the distal direction and toward the tip of the guidewire. External to the body would be a handle mechanism 17 providing an actuation force to the distal portion of the catheter. This actuation could be a rotational knob 19 translating a rotation movement to a screw mechanism providing a tension to a wire connected to the catheter tip. Other methods could include an electrical signal to drive a motion or hydraulic actuation to translate a force.
Figure 13:
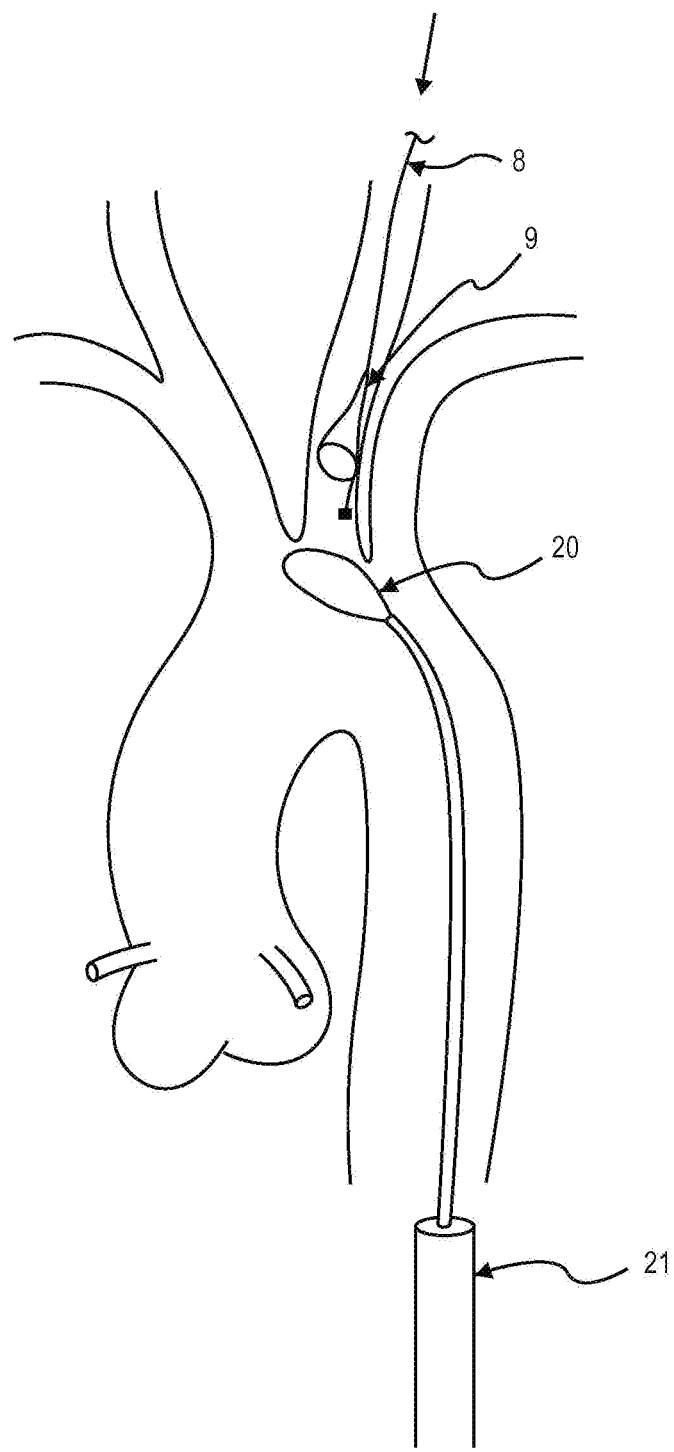
FIG. 13 illustrates a filter 9 delivered over the guidewire 8 from the carotid artery in a retrograde approach just short of the aortic arch. Once the procedure is completed the filter can be snared with a conventional snare 20 to remove it from the body. This will allow for a very small (0.03 inch) entry port in the neck to introduce the device and a larger recovery sheath 21 in the groin where other devices are introduced.
Figure 14:
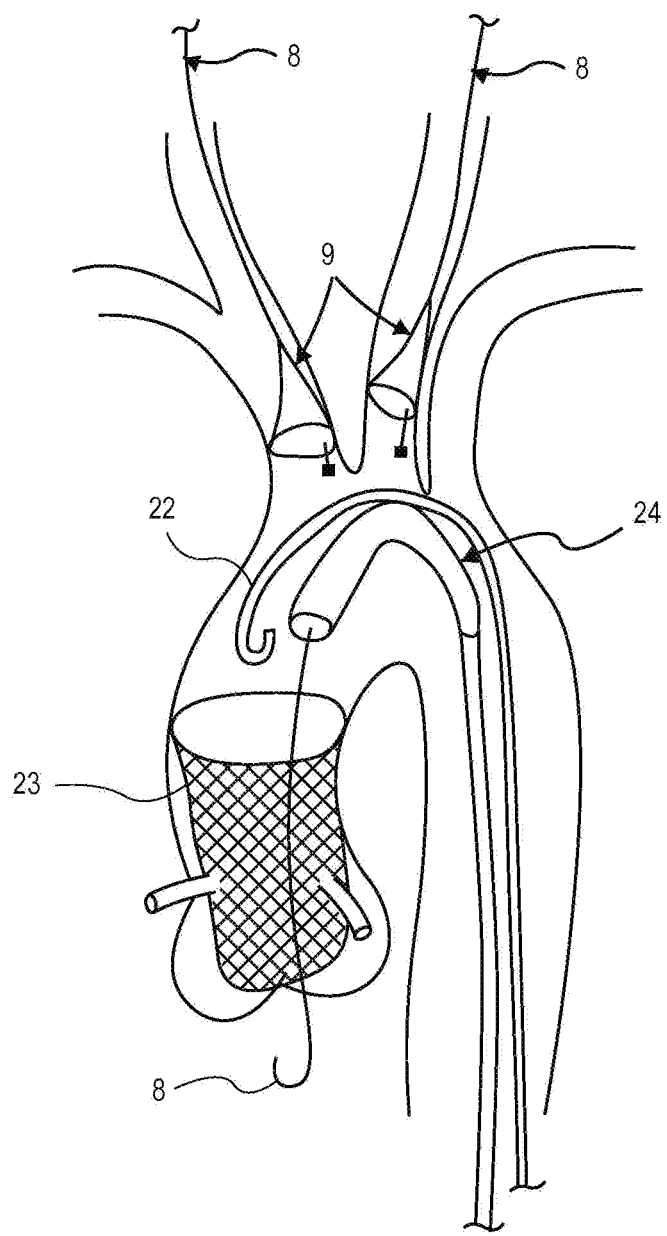
FIG. 14 illustrates a set of filters in the carotid arteries delivered and ready for additional procedures to occur under filtered protection. During a percutaneous heart valve delivery there may be multiple catheters in the aortic arch consuming much of the available area. Shown here is a pigtail catheter 22 and a delivery catheter 24 for a percutaneous heart valve 23 all within the aortic arch. The filters 9 are clear of the aortic space and will not interfere with delivery or withdrawal of these catheters.
Figure 15:
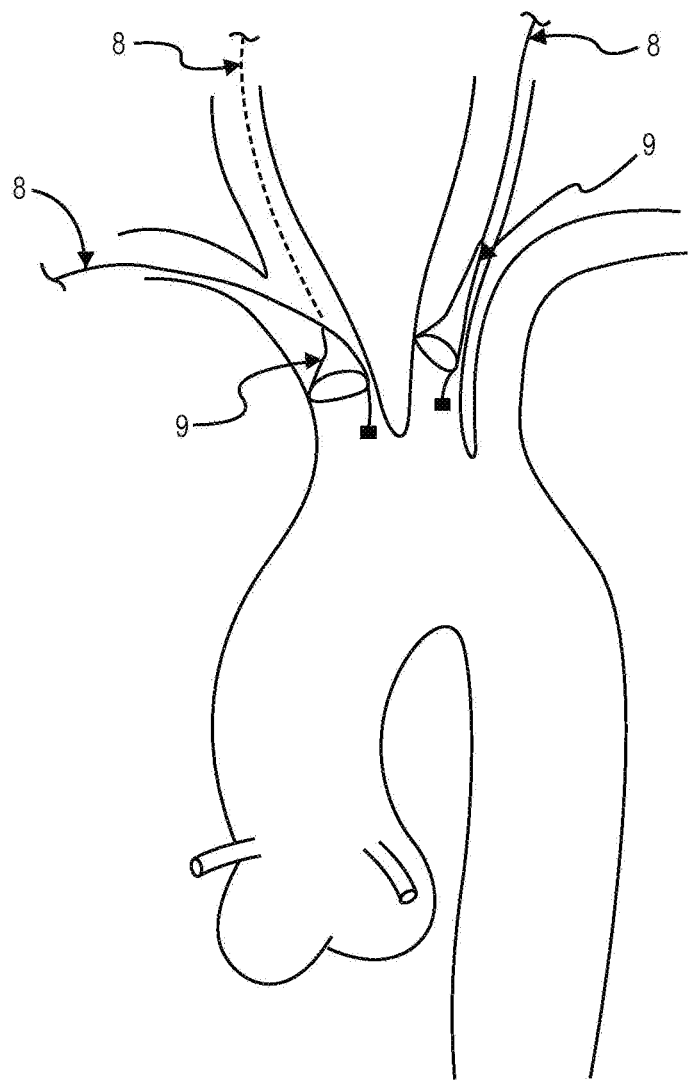
FIG. 15 illustrates another delivery pathway for the placement in the carotid or brachiocephalic trunk. Delivery includes a guidewire 8 introduced via carotid artery or subclavian artery just short of the aortic arch leaving the arch free from interference while delivering other catheters to the heart. These filters 9 can be retrieved either through the groin or recovered back through the entry point in the carotid or subclavian artery.
Figure 16:
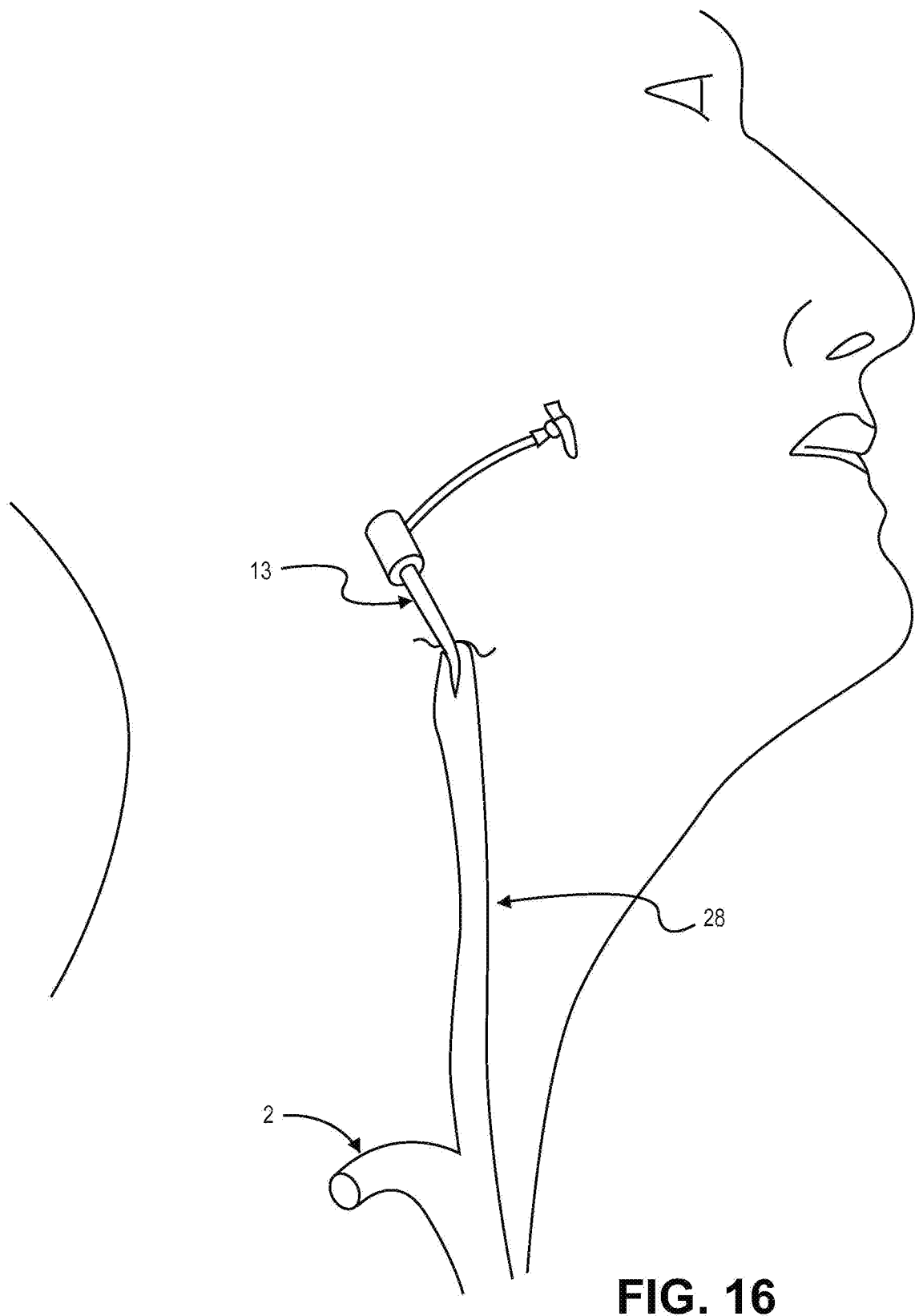
FIG. 16 illustrates a conventional entry to the carotid artery where the sheath is placed in a retrograde manner. A sheath 13 is placed into the carotid artery where access may be gained to the vasculature either anti grade or retrograde depending upon the desired placement of the device.
Figure 17:
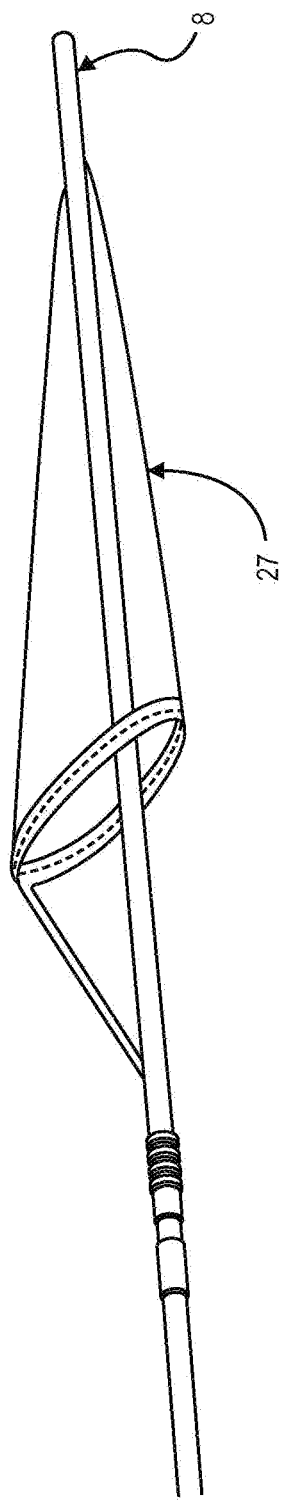
FIG. 17 illustrates an example of a common filter design where the guidewire 8 passes through the central portion of the filter 27. A memory material such as Nitinol is used to expand the filter material to the vessel wall.
Figure 18A:
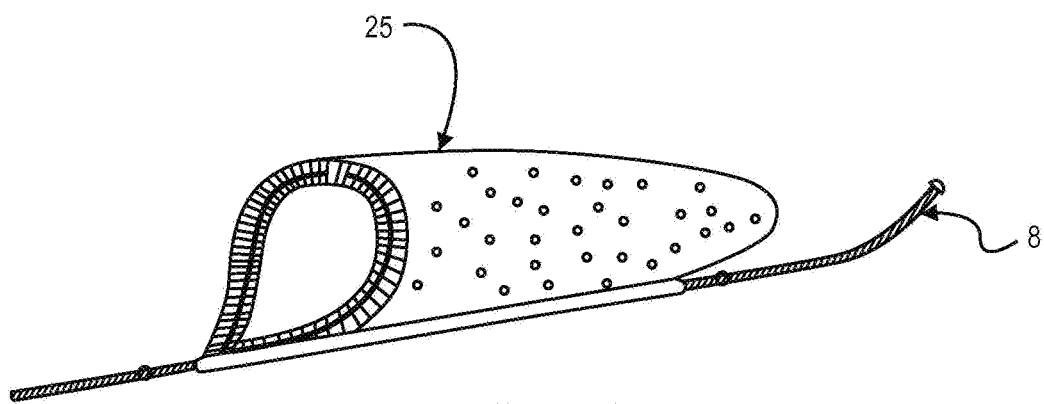
FIGS. 18A-B illustrate other examples of filters where a loop style 25 has the guidewire passing along the side of the device and functions like a wind-sox when deployed in the vessel. The other example is a framed filter where when expanded the filter material is opposed to the vessel wall and the guidewire 8 passes through the central portion of the device.
Figure 18B:
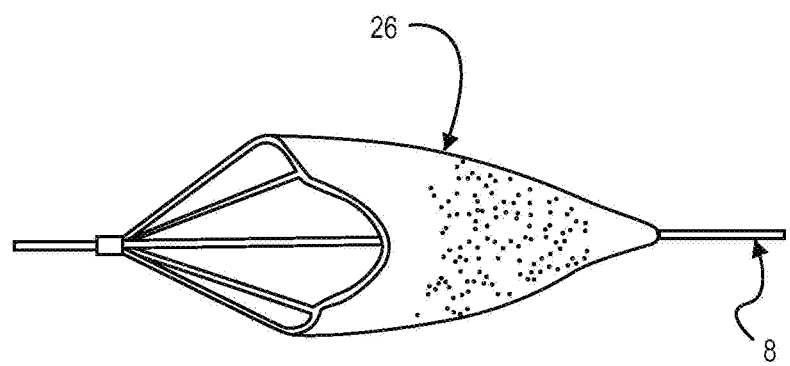

Before standard intervention would occur by a cardiologist a filter would be placed into the carotid arteries to protect the circulation to the brain where emboli could induce a stroke and leave the patient debilitated. Placement of these filters to the patient's carotid circulation would be most convenient if it occurred without obstruction of the aorta where other catheters would be passed and preferably on the patient's right side as it is common practice for the doctor to steer the catheters from this side of the table. Standard practice is to gain access in the right femoral artery where a sheath would be placed to introduce catheters, guidewires and other device delivery means. This would leave the left femoral artery open but often it too is used for other diagnostic catheters and it is less convenient to work across the patient's body. Other access sites would include carotid entry but the neck area is often again inconvenient to operate from and generally too far from the other wires and catheters. The final entry point would be an arm entry where a sheath would be placed into the brachial or radial artery for access to the subclavian artery and more distally the aorta and the carotid arteries. This approach would allow the doctor to access the patient's right arm placing a sheath into the radial artery and delivering catheters, guidewires and sheaths to the carotid arteries. After a 5 French sheath placement a guide catheter would be placed into the radial artery and advanced to the brachiocephalic trunk where the right carotid artery meets the subclavian. From here a curve in the guide catheter would allow a 180 turn to occur accessing from the brachiocephalic trunk into the aortic arch and back up the left carotid artery which is commonly found one centimeter down the aortic arch. Once the guide catheter is place a filter may be advanced into the left carotid artery and deployed leaving this vessel protected from emboli. The guide catheter could be moved proximally to leave this vasculature and back into the brachiocephalic trunk artery where a coaxial filter could now be placed protecting this carotid artery. The connection between the two filters is a common axial link where the distal or left carotid filter would be attached to a 0.014 inch guidewire as normally constructed and the more proximal filter would utilize a tubular member such as a polymer or Nitinol hypo tube. The distal filter may need to be gently engaged to the vessel wall to allow the connection guidewire to be tensioned removing any slack or loop within the aortic arch. This may be possible with engagement barbs restricting proximal motion of the device in the vessel when deployed. Other means may be a stronger force in the memory metal loop to keep the device opposed to the wall. Now the circulation to the brain is protected and the aortic arch is clear from obstruction the normal procedure can occur. Examples of these procedures include but are not limited to:

Coronary stenting
Aortic valve replacement via catheterization
Aortic or mitral valve replacement via transapical
Aortic balloon valvuloplasty
Mitral valvuloplasty
Mitral valve replacement via catheterization
Diagnostic catheterization
Surgical valve replacement (aortic or mitral)
Surgical valve repair (aortic or mitral)
Annuloplasty ring placement
Atrial fibrillation catheterization
PFO closure (surgical or catheter based)
Left atrial appendage closure (catheter or surgical)

Once the procedure has been completed the filters may be removed immediately or left in place if an antirombotic coating is added or the patient remains on blood thinning agents to limit clot from forming on the filters. It may be advantageous to leave the filters in for a period of twenty four hours as the patient begins to recover. When removal is necessary the goal is to not dislodge any trapped emboli within the filter. Conventionally this is accomplished by pulling the filter into a larger recovery sheath to first close the open end of the filter and draw the remaining portion safely back into the recovery catheter. With the filters being opposed in direction it may be advantageous to move the distal filter into the proximal filter and recover them both together in a nested orientation.

What is claimed is:

1. A method of preventing foreign material from traveling into a carotid circulation, the method comprising:
   advancing a first filter system through a right subclavian artery, the first filter system comprising a first guide catheter and a first filter;
   expanding the first filter in a right common carotid artery;
   advancing a second filter system through a left subclavian artery, the second filter system comprising a second guide catheter and a second filter; and
   expanding the second filter in a second vessel.

2. The method of claim 1, wherein when expanded, the first filter prevents foreign material from traveling into the right common carotid artery.

3. The method of claim 1, wherein when expanded, the second filter prevents foreign material from traveling into a left common carotid artery.

4. The method of claim 1, further comprising introducing the second filter through a radial entry point.

5. The method of claim 1, further comprising introducing the first filter through a radial entry point.

6. The method of claim 1, further comprising introducing the second filter through a brachial entry point.

7. The method of claim 1, further comprising introducing the first filter through a brachial entry point.

8. The method of claim 1, further comprising curving the first filter system to access the right common carotid artery.

9. The method of claim 1, further comprising curving the second filter system to access the second vessel.

10. The method of claim 1, further comprising introducing the first filter into the right common carotid artery using a guidewire.

11. The method of claim 1, further comprising introducing the second filter into the second vessel using a guidewire.

* * * * *